United States Patent [19]

deLaszlo et al.

[11] Patent Number: 5,292,741

[45] Date of Patent: Mar. 8, 1994

[54] MACROCYCLES INCORPORATING QUINAZOLINONES

[75] Inventors: Stephen E. deLaszlo, Atlantic Highlands; Tomasz Glinka, Westfield; Robert B. Nachbar, Washington Crossing; Eric E. Allen, Somerset, all of N.J.; Kristine Prendergast, Doylestown, Pa.

[73] Assignee: Merck & Co., Inc., Rahway, N.J.

[21] Appl. No.: 931,749

[22] Filed: Aug. 18, 1992

[51] Int. Cl.$^5$ .................. C07D 515/18; C07D 515/22; A61K 31/395; A61K 31/38
[52] U.S. Cl. .................. 514/257; 514/293; 514/183; 540/456; 540/472
[58] Field of Search ............... 514/281, 293, 257, 183; 540/456, 472

[56] References Cited

FOREIGN PATENT DOCUMENTS 411766 2/1991 European Pat. Off. ............ 544/287
445811 9/1991 European Pat. Off. ............ 544/287

Primary Examiner—Robert T. Bond
Attorney, Agent, or Firm—Robert J. North; Mark R. Daniel; Joseph F. DiPrima

[57] ABSTRACT

Macrocyclic compounds of general Structure I:

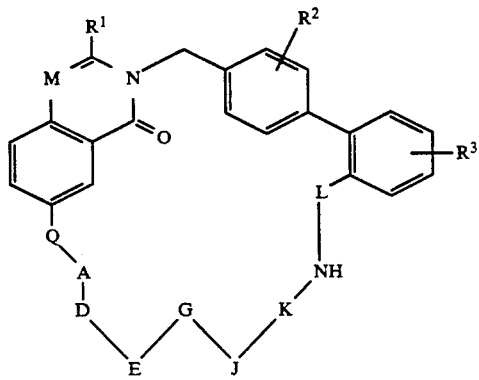

Wherein M is C or N are angiotensin II receptor (A-II) antagonists useful in the treatment of certain cardiovascular dysfunctions and ocular hypertension.

10 Claims, No Drawings

MACROCYCLES INCORPORATING QUINAZOLINONES

SUMMARY OF THE INVENTION

This invention is concerned with novel compounds of general structural formula I:

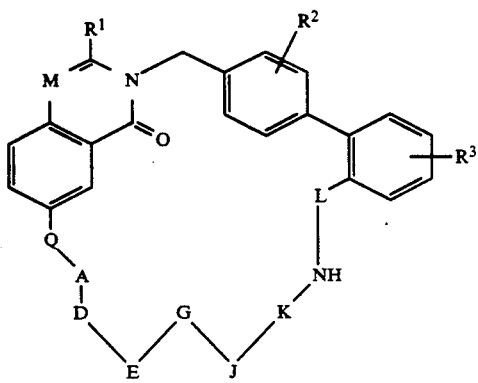

wherein M is C or N which are A-II antagonists.

The invention is also concerned with pharmaceutical formulations comprising one or more of these novel compounds as active ingredient or in combination with other active ingredients.

The invention is further concerned with the method of treating cardiovascular disease such as hypertension, and congestive heart failure and ocular hypertension and glaucoma associated therewith by administration of a novel compound or novel pharmaceutical formulation of this invention.

The invention is also concerned with novel processes useful for the synthesis of the novel compounds of the invention.

BACKGROUND OF THE INVENTION

Renin-angiotensin system (RAS) plays a central role in the regulation of normal blood pressure and seems to be critically involved in hypertension development and maintenance as well as congestive heart failure. Angiotensin II (A II), an octapeptide hormone is produced mainly in the blood during the cleavage of angiotensin I by angiotensin converting enzyme (ACE) localized on the endothelium of blood vessels of lung, kidney and many other organs and is the end product of the RAS. A II is a powerful arterial vasoconstricter that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors but their experimental and clinical applications have been limited by the partial agonist activity and lack of oral absorption [M. Antonaccio. *Clin. Exp. Hypertens.* A4, 27–46 (1982); D. H. P. Streeten and G. H. Anderson, Jr.—*Handbook of Hypertension, Clinical Pharmacology of Antihypertensive Drugs,* ed. A. E. Doyle, Vol. 5, pp. 246–271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; 4,582,847; and 4,880,804; in European Patent Applications 028,834; 245,637; 253,310; 291,969; 323,841; 324,377 and 380,959; and in articles by A. T. Chiu, et al. [*Eur. J. Pharm. Exp. Therap,* 157, 13–21 (1988)] and by P. C. Wong, et al. [*J. Pharm. Exp. Therap,* 247, 1–7 (1988): *Hypertension,* 13, 489–497 (1988)]. All of the U.S. Patents, European Patent Applications 028,834 and 253,310 and the two articles disclose substituted imidazole compounds which are generally bonded through a lower alkyl bridge to a substituted phenyl. European Patent Application 245,637 disclosed derivatives of 4,5,6,7-tetrahydro-2H-imidazo [4,5-c]-pyridine-6-carboxylic acid and analogs thereof as antihypertensive agents.

In addition to the foregoing, EP 411,766 describes substituted quinazolinones with A-II antagonist activity and WO 91/15209 describes pyridopyrimidines with A-II antagonist activity.

DETAILED DESCRIPTION

The novel compounds of the invention are represented by structural formula I:

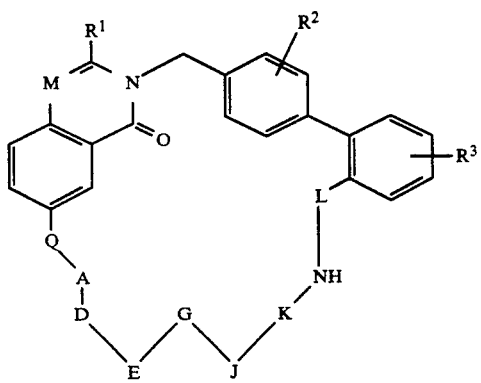

or a pharmaceutically acceptable salt thereof, wherein:
the chain A-D-E-G-J comprises 4–10 atoms;
Q is —N($R^4$)— or

$R^1$ is
a) aryl,
b) $C_{1-6}$ alkyl or $C_{2-5}$ alkenyl, each of which is unsubstituted or substituted with aryl, $C_{3-7}$ cycloalkyl, halo, $CF_3$ or $CF_2CF_3$,
c) $C_{3-7}$ cycloalkyl, or
d) perfluoro $C_{1-4}$ alkyl;
$R^2$ is $C_{1-6}$ alkyl or F;
$R^3$ is
a) H,
b) $C_{1-6}$ alkyl,
c) aryl,
d) heteroaryl,
e) $C_{1-4}$ alkylamino,
f) di($C_{1-4}$ alkyl)amino,
g) ($C_{1-6}$ alkoxy)$CH_2$—,
h) ($C_{1-6}$ alkylthio)$CH_2$—,
i) $C_{1-6}$ alkylthio,
j) ($C_{1-6}$ alkyl)$_2NCH_2$—,
k) $C_{2-6}$ alkenyl,
l) $C_{2-6}$ alkynyl, m) aryl $C_{1-6}$ alkyl—, or n) $C_{3-7}$ cycloalkyl;

$R^4$ is a) —$COR^6$ wherein $R^6$ is 1) aryl, 2) heteroaryl, 3) morpholinyl, 4) piperazinyl, 5) N-($C_{1-4}$ alkyl)-piperazinyl, 6) N-(aryl)piperazinyl 7) $C_{1-6}$ alkyl, or 8) substituted $C_{1-6}$ alkyl or

9) N—$(CR^1)$-piperazinyl;

b) —$CO_2R^7$ wherein $R^7$ is

1) $C_{1-6}$ alkyl 2) substituted $C_{1-6}$ alkyl, 3) aryl, or 4) heteroaryl;

c) —$CONR^7R^8$ wherein $R^8$ is $C_{1-4}$ alkyl or H;

d) $C_{1-6}$ alkyl, e) substituted $C_{1-6}$ alkyl, f) aryl, g) heteroaryl or h) hydrogen;

M is —N= or

wherein $R^9$ is H, $C_{1-3}$ alkyl, F or $CF_3$;

K is —CO— or —$SO_2$—;

L is —CO— or —$SO_2$—

A is —CO—, or —$CH_2$—;

D is —$CH_2$—, —O—, —$NR^8$ or a single bond;

E is $(CH_2)_b$ wherein b=0–6;

G is (a) —$C(R^5)_2$—, wherein the $R^5$ groups are the same or different and $R^5$ is $C_{1-6}$ alkyl, substituted $C_{1-6}$ alkyl, aryl, heteroaryl or hydrogen (b) —O—, (c) —$S(O)_p$— wherein p is 0–2, (d) —CH=CH—, (e) —CO—, (f) —$NR^5CO$—, (g) —$NHSO_2NH$—, (h) —$CO_2$—, (i) —OCONH—, (j) —$NHCO_2$—, (k) —$NR^7$, (l) aryl, (m) heteroaryl, or (n) single bond;

J is (a) $(CH_2)_r$ wherein r is 1–8, or (b) single bond with the provisos that:

1) if A is CO then $R^4$ is $C_{1-6}$ alkyl, substituted $C_{1-6}$ alkyl, aryl, heteroaryl or H;

2) if A is CO and D is O or $NR^8$ then:

(a) E is$(CH_2)_n$ wherein n is 2–6;

(b) E is $CH_2$ and G is —$C(R^5)_2$—; or (c) E is a single bond and G is aryl or heteroaryl;

3) if A is —$(CH_2)$—, then $R^4$ is —$COR^6$, —$CO_2R^7$, —$CONR^7R^8$ or H, and D is —$CH_2$— or a single bond;

4) if Q is piperazine then A is CO.

In the foregoing description and in the remainder of this specification the various terms are defined as follows.

The term "halo" or "halogen" includes Cl, Br, F and I.

The terms "alkyl", "alkenyl", alkynyl" and the like include both the straight chain and branched chain species of these generic terms wherein the number of carbon atoms in the species permit. Unless otherwise noted, the specific names for these generic terms shall mean the straight chain species. For example, the term "butyl" shall mean the normal butyl substituent, n-butyl.

The term substituted alkyl or alkenyl means alkyl or alkenyl is substituted with aryl, $C_{3-7}$ cycloalkyl, halo, $CF_3$ or $CF_2CF_3$.

The term aryl denotes phenyl or naphthyl, either unsubstituted or substituted with $C_{1-3}$ alkyl, $C_{1-3}$ alkoxy, halo, or $CF_3$.

The term heteroaryl means a 5 or 6-membered heteroaromatic comprising up to 3 heteroatoms selected from O, N and S such as imidazole, pyrazole, triazole, thiazole, oxazole, thiadiazole, oxadiazole, oxathiazole, pyridine, pyrimidine, pyrazine, pyridazine, thiazine, or the like wherein the heteroaromatic can be unsubstituted or substituted with one or two substitutents selected from $C_{1-3}$ alkyl, $C_{1-3}$ alkoxy, halo or $CF_3$.

One embodiment of the novel compounds of this invention is represented by structural formula I wherein M is N.

A class of compounds within this embodiment is that wherein L and K are independently —$SO_2$— or CO.

A subclass of compounds within this class is that wherein A is —$CH_2$— or CO—.

Exemplifying this subclass are the compounds depicted in Table I.

TABLE I

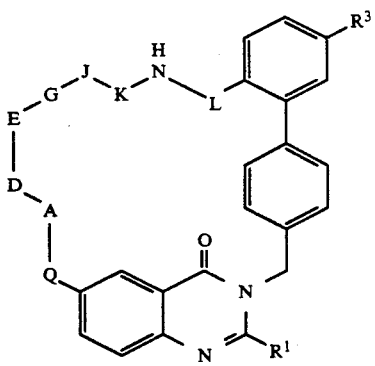

| R¹ | L | K | J | G | E | D | A | R³ | Q |
|---|---|---|---|---|---|---|---|---|---|
| Pr | SO$_2$ | CO | (CH$_2$)$_6$ | — | — | — | CH$_2$ | Pr | N—CBz |
| Pr | SO$_2$ | CO | (CH$_2$)$_6$ | — | — | — | CH$_2$ | H | N—CBz |
| Pr | SO$_2$ | CO | (CH$_2$)$_4$ | — | — | — | CH$_2$ | H | N—CBz |
| Bu | SO$_2$ | CO | (CH$_2$)$_6$ | — | — | — | CH$_2$ | H | N—CBz |
| Pr | SO$_2$ | CO | (CH$_2$)$_6$ | — | — | — | CH$_2$ | H | N—H |
| Pr | SO$_2$ | CO | (CH$_2$)$_6$ | — | — | — | CH$_2$ | H | N—Bz |
| Pr | SO$_2$ | CO | (CH$_2$)$_6$ | — | — | — | CH$_2$ | Pr | N—H |
| Pr | SO$_2$ | CO | — | — | (CH$_2$)$_5$ | NH | CO | Pr | N—H |
| Bu | SO$_2$ | CO | (CH$_2$)$_6$ | — | — | — | CO | Pr | N—H |
| Pr | SO$_2$ | CO | (CH$_2$)$_6$ | — | — | — | CO | Pr | N—Bn |
| Bu | SO$_2$ | CO | (CH$_2$)$_4$ | m-phenyl | — | — | CO | Pr | N—CH$_2$-2-Pyr |
| Pr | SO$_2$ | CO | (CH$_2$)$_4$ | m-phenyl | — | — | CH$_2$ | H | N—Bz |
| Pr | SO$_2$ | CO | (CH$_2$)$_4$ | o-phenyl | — | — | CH$_2$ | H | N—Bz |
| Pr | SO$_2$ | CO | (CH$_2$)$_4$ | p-phenyl | — | — | CH$_2$ | H | N—Bz |
| Pr | SO$_2$ | CO | — | O | (CH$_2$)$_5$ | — | CH$_2$ | H | N—CBz |
| Pr | SO$_2$ | CO | (CH$_2$)$_6$ | C(Me)$_2$ | — | — | CH$_2$ | H | N—Bz |
| Pr | SO$_2$ | CO | (CH$_2$)$_4$ | m-phenyl | — | — | CH$_2$ | H | N—Bz |
| Pr | SO$_2$ | CO | (CH$_2$)$_6$ | C(Me)$_2$ | — | — | CH$_2$ | H | N—CONHEt |
| Pr | SO$_2$ | CO | — | NH | (CH$_2$)$_5$ | — | CH$_2$ | H | N—Bz |
| Pr | SO$_2$ | CO | (CH$_2$)$_4$ | C(Me)$_2$ | CH$_2$ | — | CH$_2$ | H | N—Bz |
| Pr | SO$_2$ | CO | (CH$_2$)$_2$ | — | — | — | CO | H | pip |
| Pr | SO$_2$ | CO | (CH$_2$)$_3$ | — | — | — | CO | H | pip |
| Pr | SO$_2$ | CO | (CH$_2$)$_4$ | — | — | — | CO | H | pip |
| Pr | SO$_2$ | CO | — | m-phenyl | — | — | CO | H | pip |
| Pr | CO | SO$_2$ | (CH$_2$)$_6$ | — | — | — | CH$_2$ | Pr | N—CBz |
| Pr | CO | SO$_2$ | (CH$_2$)$_6$ | — | — | — | CH$_2$ | H | N—CBz |
| Pr | CO | SO$_2$ | (CH$_2$)$_4$ | — | — | — | CH$_2$ | H | N—CBz |
| Bu | CO | SO$_2$ | (CH$_2$)$_6$ | — | — | — | CH$_2$ | H | N—CBz |
| Pr | CO | SO$_2$ | (CH$_2$)$_6$ | — | — | — | CH$_2$ | H | N—H |
| Pr | CO | SO$_2$ | (CH$_2$)$_6$ | — | — | — | CH$_2$ | H | N—Bz |
| Pr | CO | SO$_2$ | (CH$_2$)$_6$ | — | — | — | CH$_2$ | Pr | N—H |
| Pr | CO | SO$_2$ | — | — | (CH$_2$)$_5$ | NH | CO | Pr | N—H |
| Bu | CO | SO$_2$ | (CH$_2$)$_6$ | — | — | — | CO | Pr | N—H |
| Pr | CO | SO$_2$ | (CH$_2$)$_6$ | — | — | — | CO | Pr | N—Bn |
| Bu | CO | SO$_2$ | (CH$_2$)$_4$ | m-phenyl | — | — | CO | Pr | N—CH$_2$-2-Pyr |
| Pr | CO | SO$_2$ | (CH$_2$)$_4$ | m-phenyl | — | — | CH$_2$ | H | N—Bz |
| Pr | CO | SO$_2$ | (CH$_2$)$_4$ | o-phenyl | — | — | CH$_2$ | H | N—Bz |
| Pr | CO | SO$_2$ | (CH$_2$)$_4$ | p-phenyl | — | — | CH$_2$ | H | N—Bz |
| Pr | CO | SO$_2$ | — | O | (CH$_2$)$_5$ | — | CH$_2$ | H | N—CBz |
| Pr | CO | SO$_2$ | (CH$_2$)$_6$ | C(Me)$_2$ | — | — | CH$_2$ | H | N—Bz |
| Pr | CO | SO$_2$ | (CH$_2$)$_4$ | m-phenyl | — | — | CH$_2$ | H | N—Bz |
| Pr | CO | SO$_2$ | (CH$_2$)$_6$ | C(Me)$_2$ | — | — | CH$_2$ | H | N—CONHEt |
| Pr | CO | SO$_2$ | — | NH | (CH$_2$)$_5$ | — | CH$_2$ | H | N—Bz |
| Pr | CO | SO$_2$ | (CH$_2$)$_4$ | C(Me)$_2$ | — | CH$_2$ | CH$_2$ | H | N—Bz |
| Pr | CO | SO$_2$ | (CH$_2$)$_2$ | — | — | — | CO | H | pip |
| Pr | CO | SO$_2$ | (CH$_2$)$_3$ | — | — | — | CO | H | pip |
| Pr | CO | SO$_2$ | (CH$_2$)$_4$ | — | — | — | CO | H | pip |
| Pr | CO | SO$_2$ | — | m-phenyl | — | — | CO | H | pip |
| Pr | CO | SO$_2$ | (CH$_2$)$_3$ | — | — | — | CO | Pr | pip |

CBz = carbobenzyloxy;
Bz = benzoyl;
Bn = benzyl.
O - phenyl implies

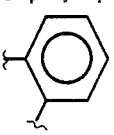

The compounds of Formula (I) can be synthesized using the reactions and techniques described below. The reactions are performed in a solvent appropriate to the reagents and materials employed and suitable for the transformation being effective. It is understood by those skilled in the art of organic synthesis that the functionality present on the heterocycle and other parts of the structure should be consistent with the chemical transformations proposed. Depending upon the reactions and techniques employed, this may involve changing the order of the synthetic steps, the use of required protecting groups followed by deprotection, and, depending upon the particular pyrimidinone fused heterocycle being formed, the use of different strategies may be employed regarding the cyclization steps and the particular starting materials utilized.

| ABBREVIATIONS USED IN REACTION SCHEMES | |
|---|---|
| Reagents: | |
| NBS | N-bromosuccinimide |
| AIBN | azo(bis)isobutyronitrile |
| DDQ | dichlorodicyanoquinone |
| Ac₂O | acetic anhydride |
| TEA | triethylamine |
| DMAP | 4-dimethylaminopyridine |
| PPh₃ | triphenylphosphine |
| TFA | trifluoroacetic acid |
| TMS-Cl | trimethylsilyl chloride |
| Im | imidazole |
| AcSK | potassium thioacetate |
| p-TsOH | p-toluenesulfonic acid |
| Solvents: | |
| Et₂O | diethyl ether |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |
| DBU | 1,8-diazabicyclo-[5.4.0]undec-7-ene |
| Me₃SnCl | trimethylstannyl chloride |
| Others: | |
| rt | room temperature |
| TBDMS | t-butyldimethylsilyl |
| OTf | OSO₂CF₃ |
| OTs | OSO₂-(4-methyl)phenyl |
| OMs | OSO₂CH₃ |
| Ph | phenyl |
| FAB-MS (FABMS) | Fast atom bombardment mass spectroscopy |
| NOE | Nuclear Overhauser Effect |
| SiO₂ | silica gel |
| trityl | triphenylmethyl. |
| s.b. | single bond |

The compounds of Formula I may be prepared via a key macrocyclisation of a precursor of structure 1. The protocol of Keck (J. Org. Chem. 50, 2394 (1985) is preferred but other similar macrocyclisation methods known to those skilled in the art may be suitable. For example, a solution of uncyclised sulphonamido carboxylic acid of structure 1 may be added to a refluxing solution of dicyclohexylcarbodiimide in dry ethanol free chloroform in the presence of DMAP and DMAP hydrochloride via a syringe pump over a period of 18 hours to give rise to macrocycles of formula I. The macrocycle may then be further modified with appropriate care for the relevant stabilities of the functional groups within the molecule.

SCHEME 1

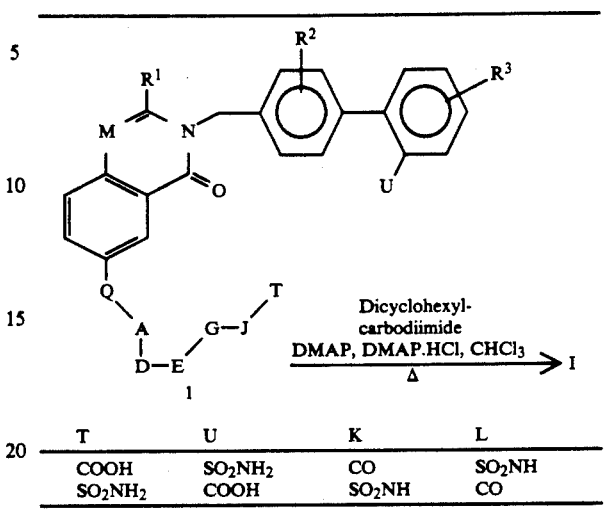

| T | U | K | L |
|---|---|---|---|
| COOH | SO₂NH₂ | CO | SO₂NH |
| SO₂NH₂ | COOH | SO₂NH | CO |

Precursors of structure 1 may be prepared from protected acids and sulphonamides 2 as indicated in Scheme 2. The choice of protecting groups are dependant on the remaining functionality in the molecule and may be made by those skilled in the art. The ester and t-butyl sulphonamide function have been found to be particularly useful as suggested in Scheme 2.

SCHEME 2

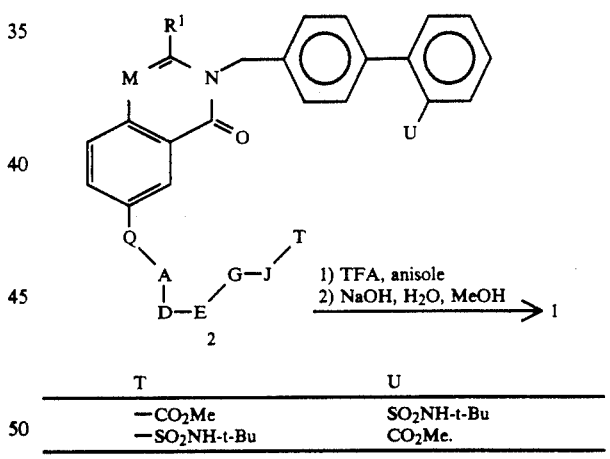

| T | U |
|---|---|
| —CO₂Me | SO₂NH-t-Bu |
| —SO₂NH-t-Bu | CO₂Me. |

In the case where Q is not piperazine, the following route may give rise to compounds of Formula 2:

A 6-nitro quinazolinone (prepared according to methods described in EP 0 411 766 A1) or 7-nitro isoquinolinone of structure 3 may be alkylated with either a bromomethylbiphenyl-2'-sulfonamide or 4-bromomethyl-2'-carboxybiphenyl, or 4-bromobenzylbromide to give structure 4 (Scheme 3). Synthesis of compounds of Formula I where A=CH₂ may then be accomplished by reduction of the nitro group followed by acylation with benzylchloroformate to give intermediate 5. In the case where compounds of Formula I have R⁴ as an amide, the acid chloride in question could be used in place of benzylchloroformate. However, 5 will give rise to a versatile synthetic intermediate for the synthesis of any analogs of interest. Alkylation of 5 under basic conditions with the linking chain of interest will give 2 (with the proviso that appropriate protecting groups must be present in the linking chain if they might interfere with the alkylation reaction) in the case where the biphenyl has been attached in the synthesis of 4. However, in the case where X=Br a coupling reaction of a suitable functionalized boronic acid or aryl stannate 6a will give 2. The choice of approach depends on the substitution pattern on the molecule in question and the ease of preparing the synthetic intermediates of interest.

If A=CO in compounds of Formula I preliminary consideration of the alkyl group $R^4$ should be made (Scheme 4). The 6-nitro quinazolinone or 7-nitro isoquinolinone 4 may be directly reduced to the amino quinazolinone by catalytic reduction in the cases where X is not bromine, otherwise dissolving metal reduction of the nitro group is the method of choice. If $R^4$ is alkyl, reductive alkylation of the nitro group in 4 or the amino group in 7 may give alkyl amino quinazolinones, 8. Alternatively, acylation of 7 with benzyl chloroformate followed by alkylation with an alkyl halide of choice

SCHEME 3

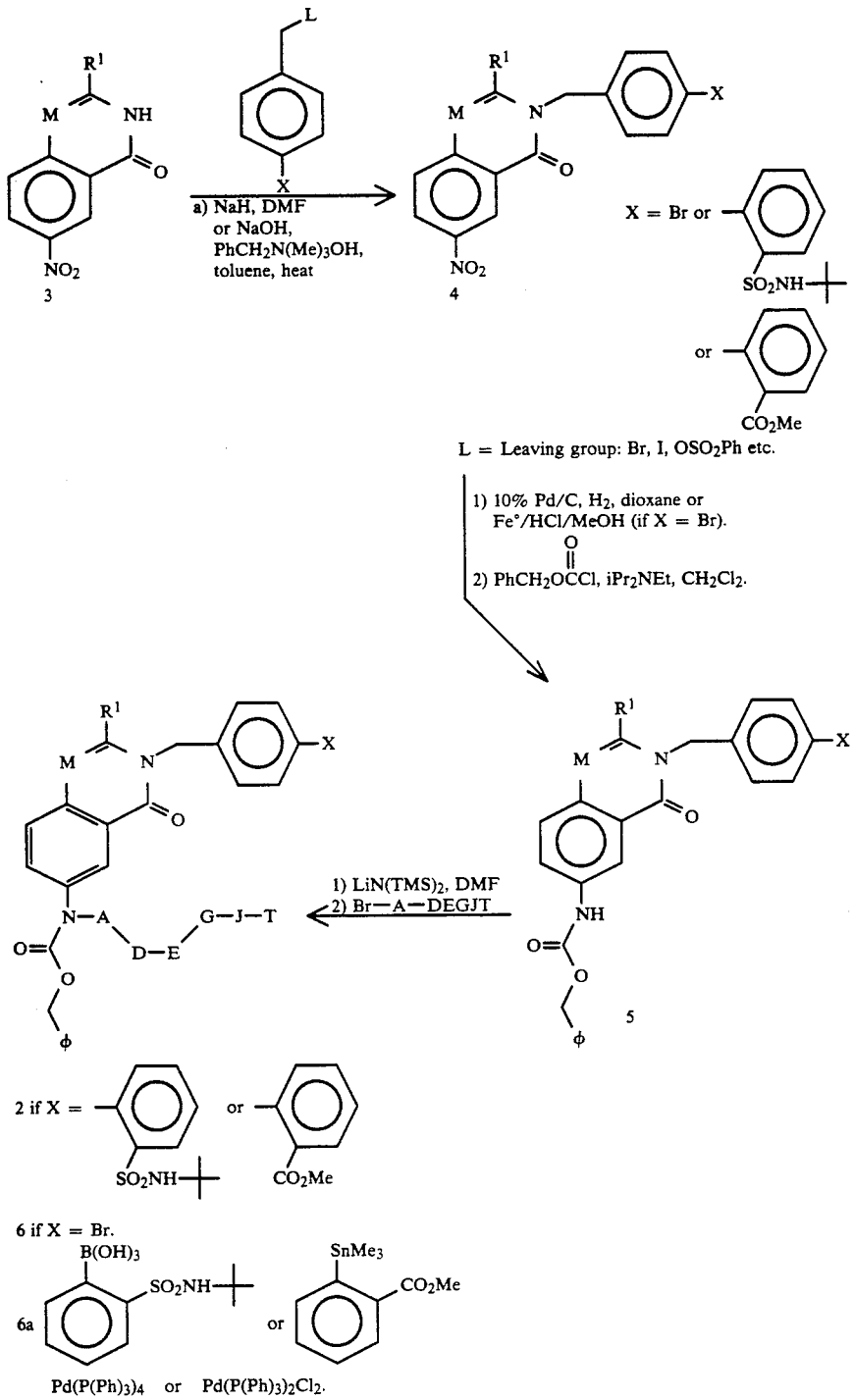

and reductive removal of the carbongenzyloxy group will give compounds of structure 8. 8 may then be acyclated with an acid chloride or isocyanate or imidoyl chloride to give either compounds of structure 9 in the case where X is a substituted aryl group or compounds of structure 9a. 9a may then be converted to 9 via coupling reactions as outlined in Scheme 3.

If A is C=O and $R^4$ is H then 4 may be directly acylated with the requisite chain to give 9 or 9a.

possible to acylate the piperazine in the presence of a deprotected sulphonamide on the biphenyl. Compound 11 may now be treated in the same manner as compound 2 or 6 for conversion into a cyclisation precursor.

SCHEME 4

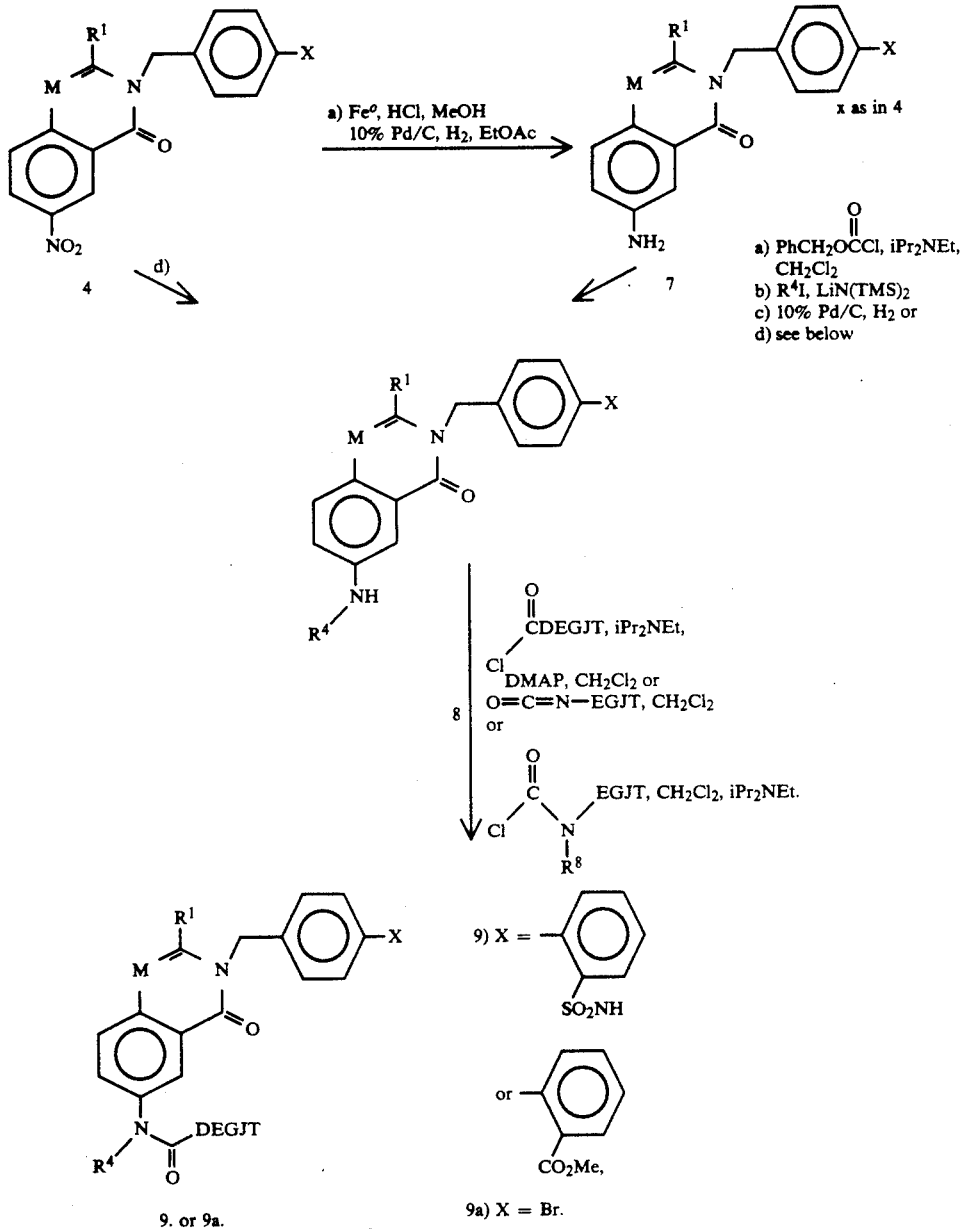

d) = $R^4$CHO, THF, NaCNBH$_3$—; or
$R^4$ CHO, H$_2$, 10% Pd/C

In the case where Q is piperazine:

Scheme 5 illustrates how a 6-piperazino quinazolinone or 7-piperazino isoquinonlinone 10 may be acylated selectively on the unsubstituted piperazine nitrogen with a suitably functionalised linker to give 11. It is

SCHEME 5

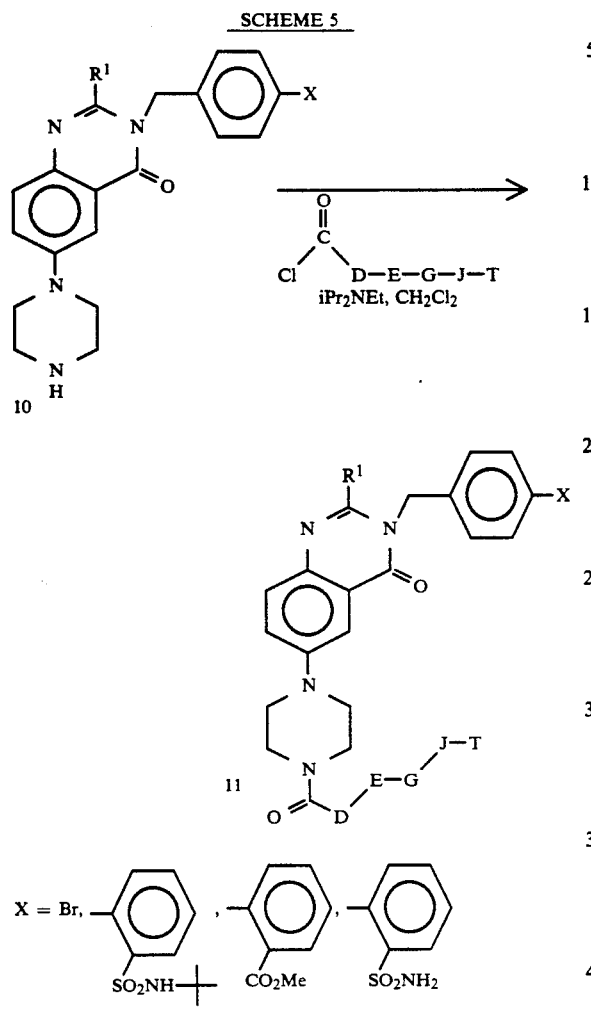

Preparation of Precursors

Biphenyl alkylating reagents 12 and 13 shown below may be prepared as described in EP O 411 766 A1.

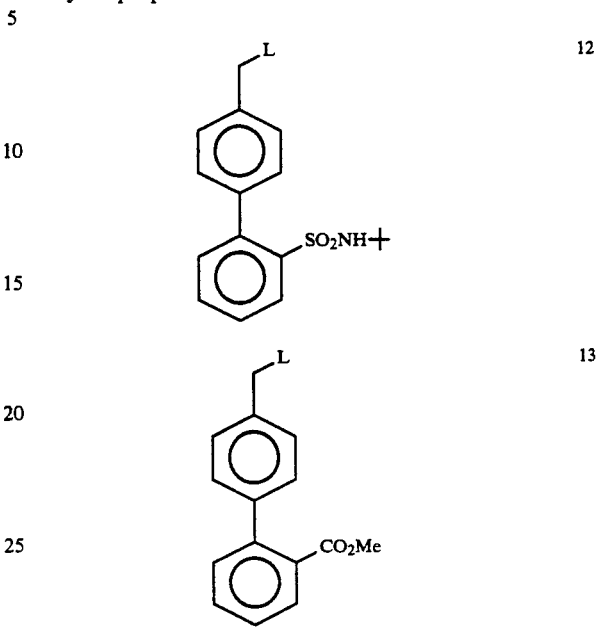

The 6-piperazino quanazolinone 10 may be prepared as outlined in Scheme 6. 5-chloro-2-nitrobenzonitrile may be reacted with N-Boc piperazine in DMF at an elevated temperature to give the aryl piperazine 14. Reduction of the nitro group followed by acylation with an acyl chloride may give the amide 15. Treatment of 15 with basic hydrogen peroxide results in cyclization to the quinazolinone 16. 16 may then be alkylated under basic conditions with a benzylic halide to give 17. The synthetic intermediate 10 is available following deprotection of the piperazine with acid.

SCHEME 6

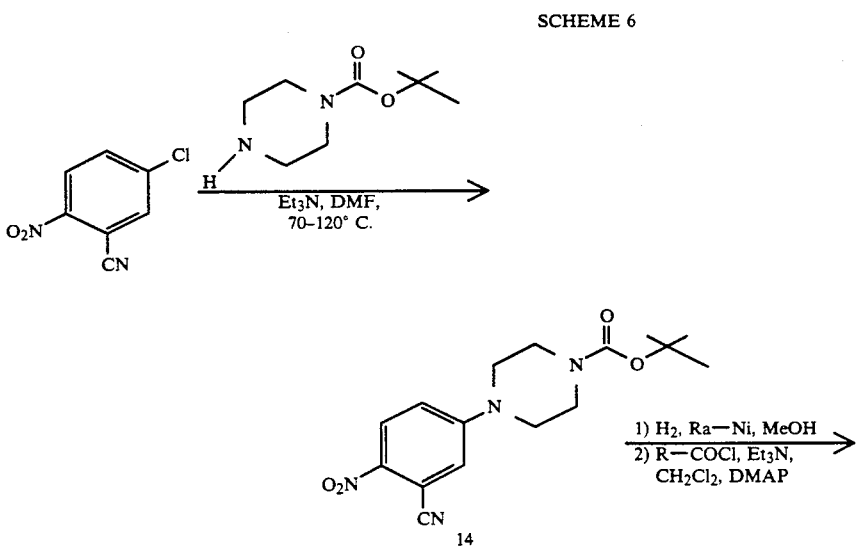

-continued
SCHEME 6
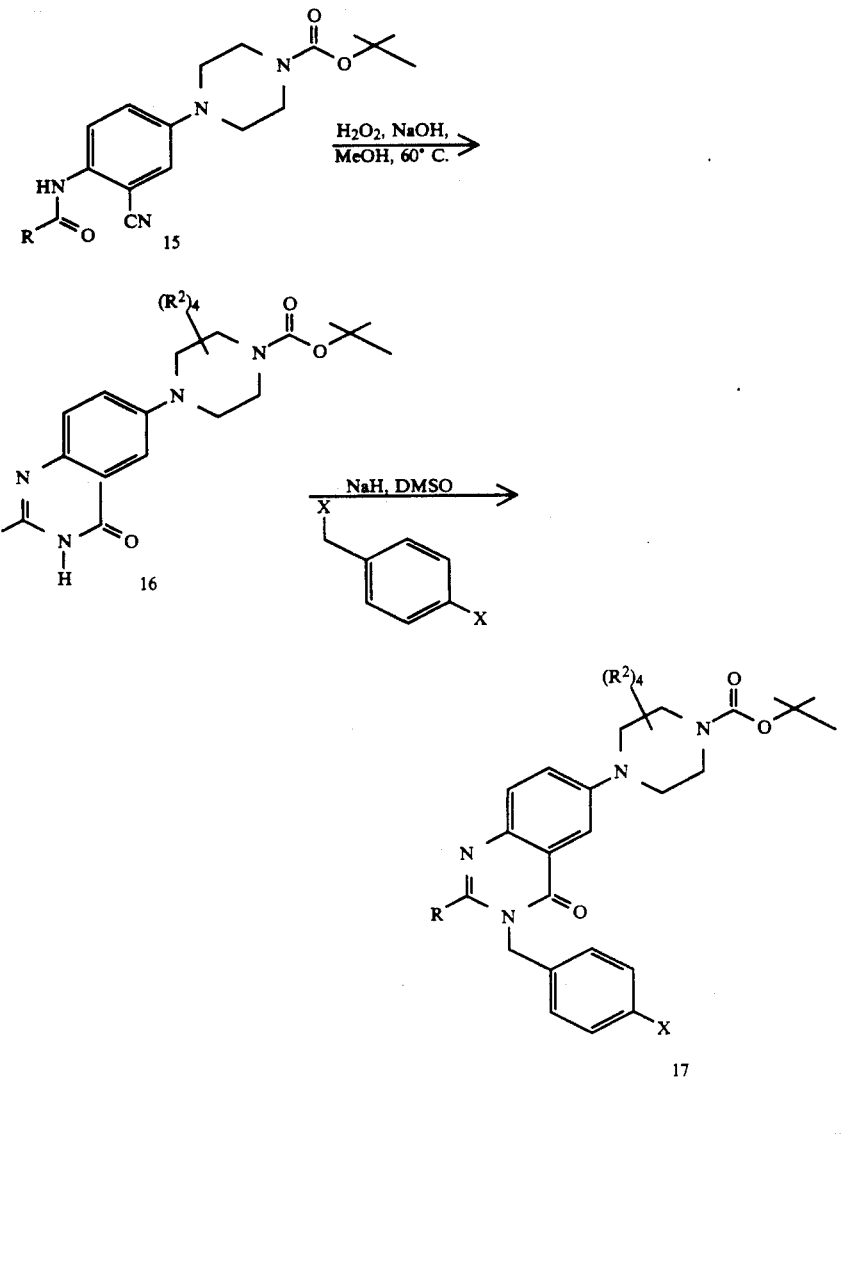
The 7-nitroisoquinolinone 3 starting materials may be prepared through a variety of routes outlined in Schemes 7–8. Suitably functionalized isocoumarins 18 may be condensed with ammonia to give isoquinolinones 3 (Scheme 7).
SCHEME 7
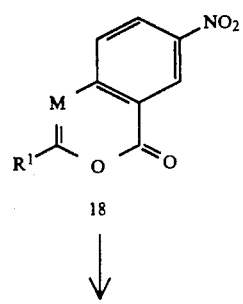

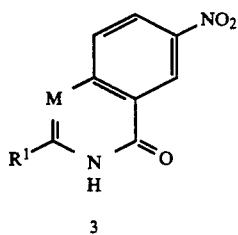

where M = CR⁹

One of the most useful methods of preparing 7-nitro-1(2H)-isoquinolinones 3 is from homophthalic anhydrides via isocoumarias 18 (Scheme 8). [R. B. Tirodkar, R. N. Usgaonkar. *Indian J. Chemistry*, 1060, 1972]. Acylation of 19 under basic conditions with anhydrides gives rise to intermediate 4-acylisochroman-1,3-diones 20. In a similar fashion the diacid 21 may also be converted to 20. Treatment of 20 with ammonia will give rise to 1(2H)-isoquinolinones 3. Alternatively, acid treatment results in decarboxylation and formation of an isocoumarin 18.

SCHEME 8

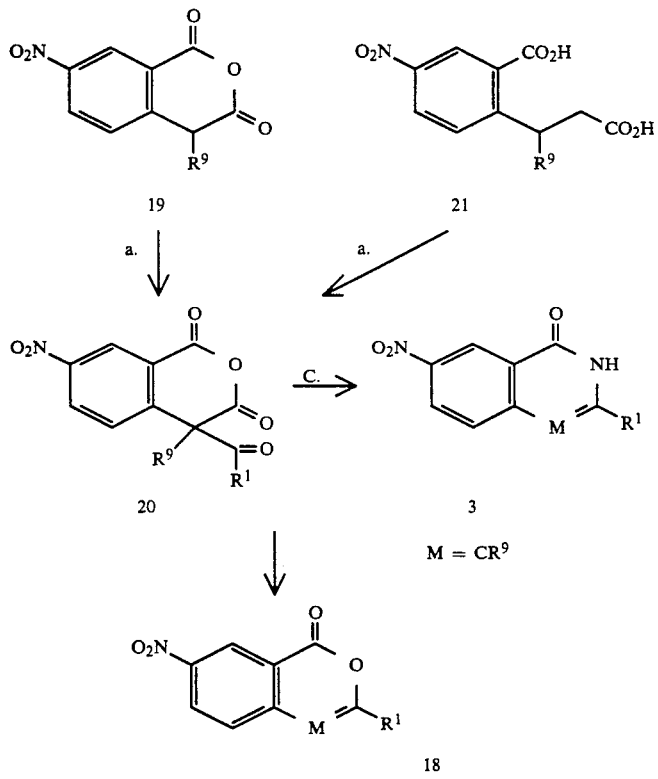

a. (R¹CO)₂O, py
b. H₂SO₄, 95° C.
c. NH₄OH provides boronic acid derivative 29 in excellent yield, after hydrolysis with dilute acid.

SCHEME 9

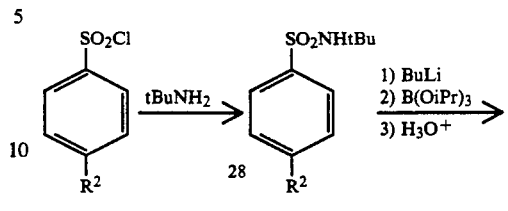

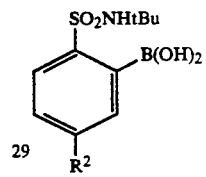

When the desired 4-substituted benzenesulfonyl chlorides are not commercially available, the necessary t-butylsulfonamide (2) derivates can be prepared using procedures outline in Scheme 10 (A-F).

SCHEME 10

The general procedure used to prepare many of the boronic acid derivatives 6a is illustrated in Scheme 9. Commercially available 4-substituted benzenesulfonyl chlorides (R²=i-Pr, n-BuO, tert amyl, Me, Et, N-Pr, t-Bu) are reacted with t-BuNH₂ to provide derivative 28 in good yield. Dianion generation, with 2.5 equivalents of n-BuLi, followed by quench with triisopropyl borate

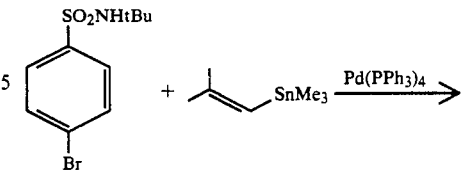

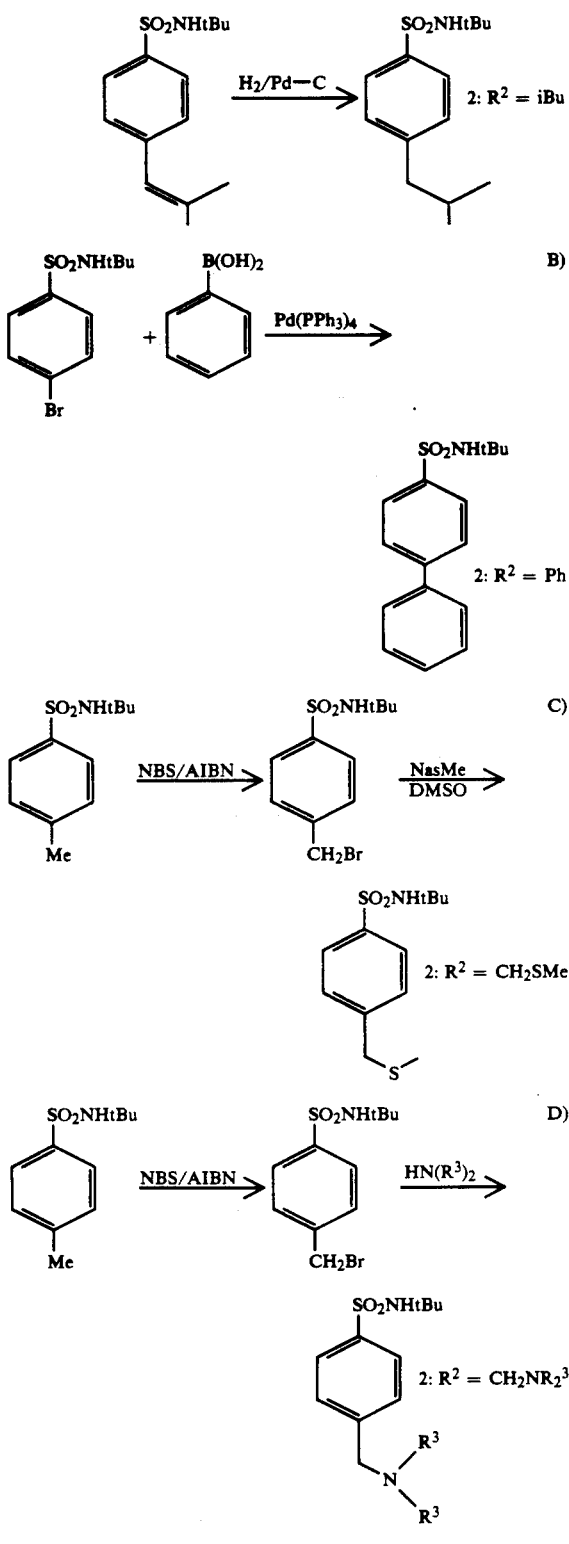

It will be appreciated by those skilled in the art that functional group transformations can be conducted on aryl and heterocyclic rings to afford desired analogs. For example, esters may be converted to amides by heating them with amines and an amide nitrogen if present in the heterocycle may be alkylated using bases such as sodium hydride in DMF with the appropriate alkyl halide. Functional group protection throughout these syntheses will be chosen to be compatible with subsequent reaction conditions. Ultimately such protecting groups will be removed to generate the desired optimally active compounds of Formula I. For example, carboxyl is often protected as its t-butyl ester which in the last step is removed by treatment with trifluoroacetic acid. Aqueous acetic acid at room temperature overnight is a preferred method to remove a trityl protecting group to liberate an $R^1$ tetrazole group.

The compounds of this invention form salts with various inorganic and organic acids and bases which are also within the scope of the invention. Such salts include ammonium salts, alkali metal salts such as sodium and potassium salts, alkaline earth metal salts such as the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methane-sulfonic, toluene-sulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor binding assay using rabbit aortae membrane preparation:

Three frozen rabbit aortae (obtained from Pel-Freeze Biologicals) were suspended in 5 mM Tris-0.25M Sucrose, pH 7.4 buffer (50 ml) homogenized, and then centrifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitration and the suspension was used for 100 assay tubes. Samples tested for screening were done in duplicate. To the membrane preparation (0.25 ml) there was added $^{125}$I-Sar$^1$Ile$^8$-angiotensin II [obtained from New England Nuclear] (10 μl; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^{125}$I-Sar$^1$Ile$^8$-angiotensin II was presented as a measure of the efficacy of such compounds as AII antagonists.

Receptor assay using Bovine adrenal cortex preparation

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethane sulfonyl fluoride (PMSF)(0.1 mM)]. (For screening of compounds, generally duplicates of tubes are used). To the membrane preparation (0.5 ml) there was added 3H-angiotensin II (50 mM) (10 μl) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound 3H-angiotensin II was presented as a measure of the efficacy of such compounds as AII antagonists.

Receptor assay using rat brain membrane preparation

Membranes from rat brain (thalamus, hypothamus and midbrain) were prepared by homogenization in 50 mM Tris HCl (pH 7.4), and centrifuged at 50,000×g. The resulting pellets were washed twice in 100 mM NaCl, 5 mM $Na_2$•EDTA, 10 mM $Na_2HPO_4$ (pH 7.4) and 0.1 mM PMSF by resuspension and centrifugation. For binding assays, the pellets were resuspended in 160 volumes of binding assay buffer (100 mM NaCl, 10 mM $Na_2HPO_4$, 5 mM $Na_2$•EDTA, pH 7.4, 0.1 mM PMSF, 0.2 mg/ml soybean trypsin inhibitor, 0.018 mg/ml o-phenanthroline, 77 mg/ml dithiothreitol and 0.14 mg/ml bacitracin. For $^{125}$I.Ile$^8$-angiotensin II binding assays, 10 μl of solvent (for total binding), Sar$^1$,Ile$^8$-angiotensin II (1 μM) (for nonspecific binding) or test compounds (for displacement) and 10 μl of [$^{125}$I]Sar$^1$-,Ile$^8$-angiotensin II (23–46 pM) were added to duplicate tubes. The receptor membrane preparation (500 μl) was added to each tube to initiate the binding reaction. The reaction mixtures were incubated at 37° C. for 90 minutes. The reaction was then terminated by filtration under reduced pressure through glass-fiber GF/B filters and washed immediately 4 times with 4 ml of 5 mM ice-cold Tris HCl (pH 7.6) containing 0.15M NaCl. The radioactivity trapped on the filters was counted using a gamma counter.

Using the methodology described above, representative compounds of the invention were evaluated and all were found to exhibit an activity of $IC_{50} < 3$ μM against the $AT_1$ and the $AT_2$ subtype.

The antihypertensive effects of the compounds described in the present invention may be evaluated using the methodology described below: Male Charles River Sprague-Dawley rats (300–375 gm) were anesthetized with methohexital (Brevital; 50 mg/kg i.p.) and the trachea was cannulated with PE 205 tubing. A stainless steel pitching rod (1.5 mm thick, 150 mm long) was inserted into the orbit of the right eye and down the spinal column. The rats were immediately placed on a Harvard Rodent Ventilator (rate—60 stokes per minute, volumn—1.1 cc per 100 grams body weight). The right carotid artery was ligated, both left and right vagal nerves were cut, and the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered, and 15 minutes later propranolol (1 mg/kg i.v.). Thirty minutes later antagonists of the Formula I were administered intravenously or orally. Angiotensin II was then typically given at 5, 10, 15, 30, 45 and 60 minute intervals and every half hour thereafter for as long as the test compound showed activity. The change in the mean arterial blood pressure was recorded for each angiotensin II challenge and the percent inhibition of the angiotensin II response was calculated.

The compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperclasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Perferably, the dosage range will be about 2.5 to 250 mg. per patient per day; more preferably about 5 to 150 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250-350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced sterotypy model. A clinically useful antipsychotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Preferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptylphysostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, and nootropic agents such as piracetam.

In order to achieve optimal anxiolytic activity, the compounds of this invention may be combined with other anxiolytic agents such as alprazolam, lorazepam, diazepam, and busipirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg.), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the unit dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples further illustrate the preparation of the compounds of Formula I and their incorporation into pharmaceutical compositions and, as such, are not to be considered or construed as limiting the invention recited in the appended claims.

I: PREPARATION OF STARTING MATERIALS

EXAMPLES I-1

6-Nitro-2-propylquinazolin-4(1H)-one

To a solution of 16.3 g (0.1 mol) of 2-amino-5-nitrobenzonitrile in 200 ml of $CH_2Cl_2$ at 0° C. was added 21 ml (0.15 mol) of triethyl amine followed by 0.3 g of DMAP and 11.71 g (0.11 mol) of butyryl chloride. The reaction mixure was warmed to room temperature and then heated over night at 50° C. The solution was washed with 1N HCl (1×20 ml), water (1×20 ml), saturated $NaHCO_3$ (2×20 ml) and brine (1×20 ml) and dried over $MgSO_4$. The solution was filtered and concentrated in vacuo. The residue was dissolved in 200 ml of MeOH to which was added 44 ml (0.22 mol) of 5M NaOH solution followed by the dropwise addition of 25 ml (0.22 mol) 30% $H_2O_2$ and 50 ml of water. The mixture was refluxed for 4 hours, cooled and filtered. The filtrate was acidified with 1N HCl and the resulting precipitate recovered by filtration. The residue was recrystalized from MeOH to give 8.3 g (0.036 mol) of pale brown fluffy crystals. $^1$H-NMR ($CDCl_3$): 1.10 (t, 3H, J=7.4 Hz), 1.93 (m, 2H), 2.79 (3 line m, 2H, J=7.3 Hz), 7.80 (d, 1H, J=8.9 Hz), 8.55 (dd, 1H, J=2.5, 8.8 Hz), 9.14 (bs, 1H).

II: PREPARATION OF PRECURSORS OF EXAMPLES WHEREIN Q=N, A=$CH_2$

EXAMPLE II-1

Step A

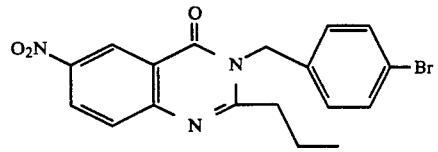

A solution of 10 g (43 mmol) of 6-nitro-2-propylquinazolinone and 11.75 g (47 mmol) of 4-bromomethyl-bromobenzene and 23.5 ml (47 mmol) of 2M NaOH and 8.9 ml of 40% benzyl trimethyl ammonium hydroxide in MeOH in 50 ml of toluene was heated at 90° C. with rapid stirring for 18 hours. The reaction mixture was diluted with 100 ml of EtOAc and was washed with water (3×30 ml), brine (2×30 ml) and was dried over MgSO4. The residue was stirred for 6 hours in 50 ml of trifluoroacetic acid in the presence of 3 ml of anisole to hydrolyze any O alkylated product. The solution was concentrated in vacuo and the residue was dissolved in 100 ml of EtOAc and was washed with saturated NaHCO3 (5×25 ml), brine (1×25 ml) and was dried over MgSO4, filtered and concentrated in vacuo. The residue was diluted with 50 ml of MeOH and stirred over night. The residue was collected by filtration, washed with MeOH and dried in vacuo to give 7.76 g of a tan solid. 45% yield. $^1$H-NMR (CDCl3-200 MHz): 1.02 (t, 3H, J=7.3 Hz), 1.85 (m, 2H), 2.74 (t, 2H, J=7.3 Hz), 5.36 (bs, 2H), 7.08 (d, 2H, J=8.3 Hz), 7.47 (d, 2H, J=7.7 Hz), 7.77 (d, 1H, J=8.9 Hz), 8.53 (dd, 1H, J=2.6, 8.9 Hz), 9.17 (d, 1H, J=2.6 Hz).

Step B

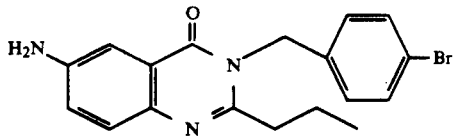

To a suspension of 8.0 g (20 mmol) of product from Step A in 100 ml of MeOH was added 8.6 ml of concentrated HCl followed by 4.4 g (80 mmol) of iron powder added at such a rate so as to maintain a gentle reflux. The reaction mixture was stirred for 90 minutes at reflux and was then poured into 600 ml of water. The suspension was made basic by addition of concentrated NH4OH. The thick suspension was filtered and the residue was washed with 4×50 ml of EtOAc with vigorous trituration. The organic phase of the filtrate was separated and the aqueous phase was extracted with EtOAc (4×100 ml). The combined organic phases were washed with water (2×100 ml), brine (1×100 ml) and then dried over MgSO4, filtered and concentrated in vacuo to give the desired product. Recovered 6.65 g. $^1$H-NMR (CDCl3-400 MHz): 0.95 (t, 3H, J=7.4 Hz), 1.73 (m, 2H), 2.61 (t, 2H, J=7.7 Hz), 3.91 (bs, 2H), 5.28 (bs, 2H), 7.01 (d, 2H, J=8.5 Hz), 7.07 (dd, 1H, J=2.7, 8.6 Hz), 7.37–7.48 (m, 4H).

Step C
Preparation of

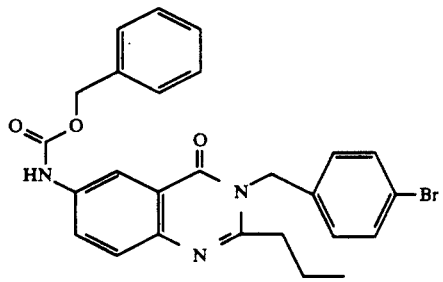

3.2 g (8.6 mmol) of product from Step B was suspended in 20 ml of dichoroethane and was treated with 2.5 ml (19.5 mmol) of diisopropylamine, 20 mg DMAP followed by 2.2 g (13 mmol) benzylchloroformate. The reaction mixture was stirred for 4 hours and was then diluted with 100 ml of CH2Cl2. The solution was washed with water (3×25 ml), brine (1×25 mL) and was dried over MgSO4, filtered and concentrated in vacuo. The residue was recrystalised from EtOAc to give a white powder. $^1$H-NMR (CDCl3-400 MHz): 0.96 (t, 3H, J=7.3 Hz), 1.76 (m, 2H), 2.62 (t, 2H, J=7.3 Hz), 5.16 (s, 2H), 5.23 (bs, 2H), 6.96 (d, 2H, J=7.4 Hz), 7.3–7.42 (m, 6H), 7.60 (m, 2H), 8.11 (m, 2H).

Step D
Preparation of

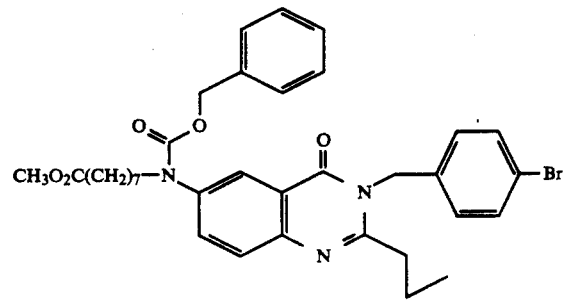

A solution of 3.0 g (5.9 mmol) of product from Step C in 15 ml of dry DMF under N2 was treated at 0° C. with 6.55 ml of 1M lithium hexamethyldisilazide in hexanes. The reaction mixture was stirred for 10 minutes and then was added a solution of 1.55 g (6.55 mmol) of methyl 6-bromooctanoate in 5 ml of dry DMF. The reaction mixture was allowed to warm to room temperature and was stirred over night. The reaction mixture was diluted with 200 ml of EtOAc, washed with water (3×50 ml), brine (1×50 ml) and was dried over MgSO4, filtered and concentrated in vacuo. The residue was purified by flash chromatography over silica gel eluting with 2% MeOH/CH2Cl2 to give 3.48 g of a brown oil. 89% yield. $^1$H-NMR (CDCl3-200 MHz): 0.99 (t, 3H, J=7.43 Hz), 1.26 (bs, 6H), 1.52 (bs, 4H), 1.80 (m, 2H), 2.26 (t, 2H, J=7.5 Hz), 2.69 (t, 2H, J=7.9 Hz), 3.65 (s, 3H), 3.75 (t, 2H, J=7.7 Hz), 5.16 (s, 2H), 5.33 (bs, 2H), 7.05 (d, 2H, J=8.4 Hz), 7.29 (bs, 4H), 7.45 (d, 2H, J=8.41 Hz), 7.62 (s, 2H), 8.09 (bs, 1H).

Step E
Preparation of

II-1-E-1

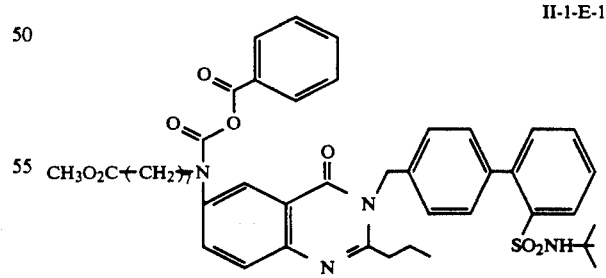

A mixture of 0.3 g (0.45 mmol) of product from Step D (0.18 g, 0.68 mmol) of 2-t-butylsulphonamidophenylboronic acid, 1.4 ml (1.76 mmol) of 1.25N NaOH, 6 ml of toluene and 1.5 ml of EtOH and 15 mg of tetrakis (triphenylphosphine) palladium [0] was heated at 95° C. for 4 hours. The reaction mixture was diluted with 20 ml of EtOAc and 5 ml of water. The aqueous phase was extracted with EtOAc (2×10 ml). The combined organic phase was washed with water (2×10 ml) and brine (1×10 ml) and dried over MgSO₄. The solution was filtered and concentrated in vacuo and the residue was purified by radial chromatography eluting with 2% MeOH/CH₂Cl₂ to give 0.30 g of an oil. 84% yield. ¹H-NMR (CDCl₃-400 MHz): 0.95 (s, 9H), 1.01 (t, 3H, J=7.4 Hz), 1.22 (bs, 6H), 1.53 (bs, 4H), 1.83 (m, 2H), 2.24 (t, 2H, J=7.65 Hz), 2.73 (t, 2H, J=7.7 Hz), 3.62 (s, 3H), 3.73 (t, 2H, J=7.5 Hz), 5.12 (s, 2H), 5.42 (bs, 2H), 7.22–7.31 (bm, 6H), 7.42–7.67 (m, 5H), 8.09 (d, 1H, J=2.6 Hz), 8.13 (dd, 1H, J=1.3, 7.9 Hz).

Employing the procedures described in Steps A through E of this Preparation but using the appropriate starting materials there were produced:

II-1-E-3

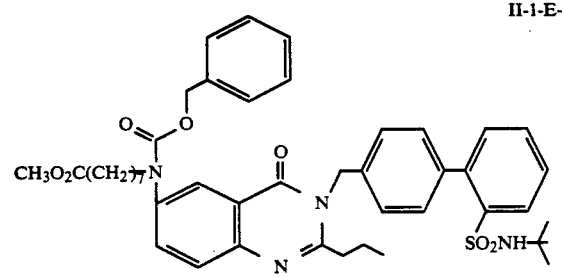

¹H-NMR (CDCl₃-400 MHz): 0.90 (t, 3H, J=7.3 Hz), 0.94 (s, 9H), 1.00 (t, 3H, J=7.4 Hz), 1.23 (m, 6H), 1.52 (m, 4H), 1.61 (m, 2H), 1.83 (m, 2H), 2.23 (t, 2H, J=7.5 Hz), 2.60 (t, 2H, J=7.7 Hz), 2.73 (t, 2H, J=7.7 Hz), 3.61 (s, 3H), 3.73 (t, 2H, J=7.7 Hz), 5.12 (s, 2H), 5.43 (s, 2H), 7.04 (d, 1H, J=1.7 Hz), 7.21–7.31 (m, 8H), 7.47 (d, 2H, 8.2 Hz), 7.55–7.62 (m, 2H), 8.01 (d, 1H, J=8.2 Hz), 8.08 (d, 1H, J=2.28 Hz).

II-1-E-3

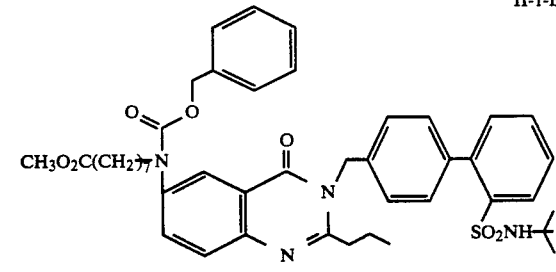

II-1-E-4

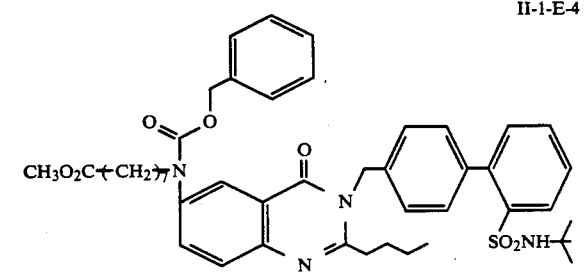

Step F
Preparation of

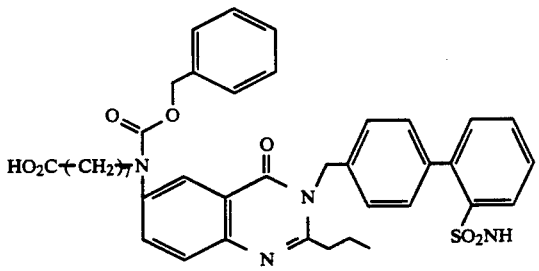

A solution of 0.3 g (0.38 mmol) of II-1-E-1 in 2 ml of TFA and 0.5 ml of anisole was stirred over night at room temperature. The reaction mixture was concentrated in vacuo and the residue was purified by radial chromatography over silica gel eluting with 4% MeOH/CH₂Cl₂ to give 0.16 g of the intermediate sulphonamide ester. The ester was stirred for 6 hours with 1 ml THF/1 ml MeOH and 1 ml of 1N NaOH. The reaction mixture was acidified with 5 ml of 1N HCl and extracted with EtOAc (3×10 ml). The organic phase was dried over MgSO₄, filtered and concentrated in vacuo. The residue was purified by radial chromatography over silica gel eluting with 6% MeOH/CH₂Cl₂ to give the title product. ¹H-NMR (CDCl₃-200 MHz): 1.02 (t, 3H, J=7.3 Hz), 1.23 (bm, 6H), 1.52 (bm, 4H), 1.82 (m, 2H), 2.28 (t, 2H, J=7.3 Hz), 2.78 (t, 2H, J=7.2 Hz), 3.75 (t, 2H, J=7.2 Hz), 4.49 (bs, 2H), 5.15 (s, 2H), 5.45 (bs, 2H), 7.22–7.71 (m, 14H), 8.10 (m, 2H).

Employing the procedure described in Step F of this preparation but using the appropriate starting materials there were produced:

II-1-F-2

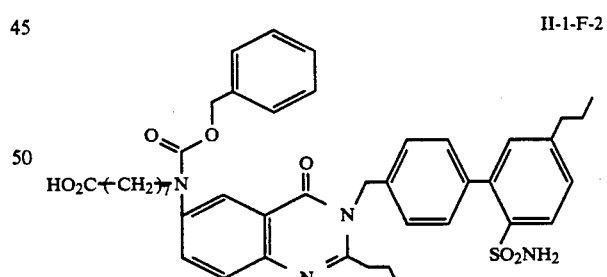

The product II-1-E-2 was deprotected in the manner described in Step F to give the title compound. ¹H-NMR (CDCl₃-200 MHz): 0.94 (t, 3H, J=7.4 Hz), 1.03 (t, 3H, J=7.3 Hz), 1.20–1.35 (m, 6H), 1.50–1.95 (m, 8H), 2.26 (t, 2H, J=7.4 Hz), 2.65 (t, 2H, J=7.8 Hz), 2.78 (t, 2H, J=7.3 Hz), 3.75 (t, 2H, J=7.4 Hz), 4.22 (s, 2H), 5.16 (s, 2H), 5.48 (s, 2H), 7.10 (d, 1H, J=1.7 Hz), 7.22–7.37 (m, 8H), 7.46 (d, 2H, J=8.2 Hz), 7.61 (m, 2H), 8.03 (d, 1H, J=8.1 Hz), 8.10 (d, 1H, J=2.3 Hz).

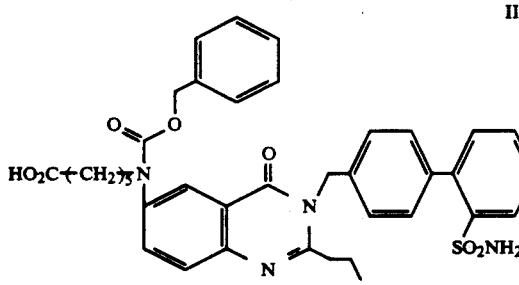

II-1-F-3

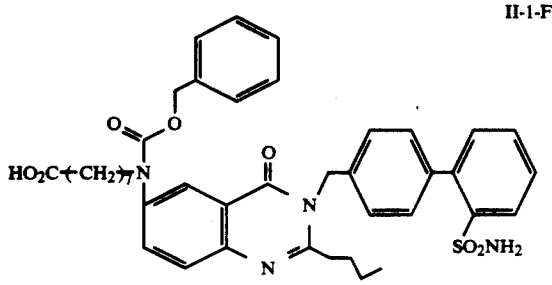

II-1-F-4

III: PREPARATION OF PRECURSORS OF EXAMPLES WHEREIN Q=N, A=CO AND D=CH₂ OR NH

EXAMPLE III-1

Step A
Preparation of

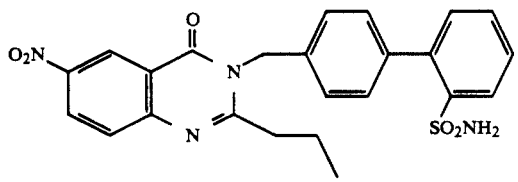

To a solution of 6-nitro-2-propyl-quinazolin-4(1H)-one (2.44 g, 6.39 mmol) and 4'-bromomethyl-biphenyl-2-tert-butyl-sulfonamide in (1.56 g, 6.71 mmol) in DMF (50 ml) powdered K₂CO₃ was added (6.0 g) and the reaction mixture was vigorously stirred for 72 hrs. The reaction mixture was diluted with water and the yellow precipitate formed was filtered and dried. To the crude intermediate anisole (1.5 ml) was added followed by the addition of TFA (25 ml). After stirring overnight at room temperature the mixture was concentrated in vacuo, the residue was dissolved in AcOEt and washed with 5% NaHCO₃. The crystalline product formed in the organic layer was filtered, washed with water and AcOEt to give the title product in form of yellow crystals. The second crop was obtained after concentrating the mother liquors. Chromatography of the mother liquors on silicagel Chromatotron plate (CH2Cl2/MeOH-30/1) furnished additional amount of the product.

¹H-NMR (CDCl₃-200 MHz): 0.92–1.08 (t, J=7.4 Hz, 3H), 1.78–1.92 (m, 2H), 2.78 (t, J=7.4, 2H), 5.47 (s, 2H), 7.18–7.62 (m, 7H), 7.80 (d, J=9.0 Hz, 1H), 8.04–8.15 (m, 1H), 8.53 (dd, J=9.0, J=2.6 Hz, 1H), 9.09 (d, J=2.6 Hz, 1H).

Step B
Preparation of

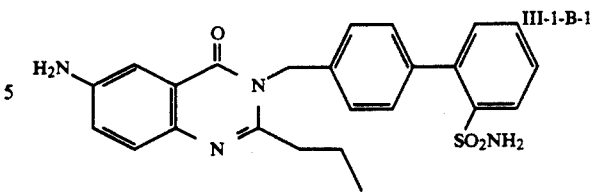

III-1-B-1

The product of Step A 1.77 g (3.70 mmol) was hydrogenated overnight under 1 atm H₂ in 50 ml dioxane in the presence of 10% paladium on carbon catalyst. The reaction mixture was filtered through Celite and the solvent was removed in vacuo to produce the crude amine as a yellow foam in quantitative yield which was used for the next step without further purification.

¹H-NMR (CDCl₃-200 MHz): 1.00 (t, J=7.4 Hz, 3H), 1.70–1.90 (m, 2H), 2.72 (t, J=7.4, 2H), 3.50 (br. s, 2H), 4.55 (br. s, 2H), 5.40 (s, 2H), 7.10 (dd, 1H, J=8.7 Hz), 7.15–7.60 (m, 9H), 8.10 (dd, J=7.7, J=1.5 Hz, 1H)

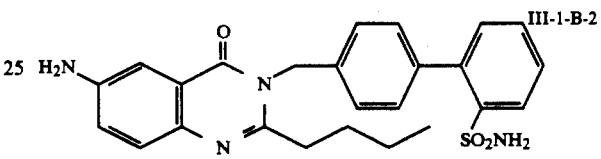

III-1-B-2

The compound III-1-B-2 was prepared in a manner analogous to that described for the 2-propyl analog starting from 6-nitro-2-propyl-quinazolin-4(1H)-one.

¹H-NMR (CDCl₃-200 MHz): 0.89 (t, J=7.4 Hz, 3H), 1.30–1.48 (m, 2H),1.62–1.78 (m, 2H), 2.70–2.83 (m, 2H), 5.42 (s, 2H), 7.14–7.25 (m, 3H), 7.35–7.60 (m, 7H), 8.04–8.10 (m, 1H).

Step C
Preparation of:

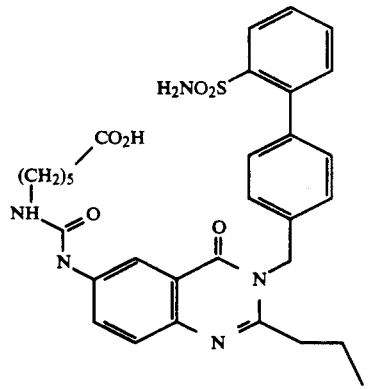

III-1-C-1

A solution of III-1-B-1 (83 mg, 0.185 mmol) and ethyl 6-isocyanatohexanoate 230 mg (1.24 mmol) in dioxane 1 ml was stirred at room temp. overnight. After removing the solvent in vacuo the residue was dissolved in 5 ml ethanol with addition of 1 ml of 10% aqueous NaOH. After 2 hrs at room temp. the reaction mixture was neutralized with 1M HCl and extracted with ethyl acetate. The title product was purified by radial chromatography on silica gel plate with CH2Cl2/MeOH-20/1.

¹H-NMR (CDCl₃/CD₃OD-200 MHz): 1.00 (t, J=7.5 Hz, 3H), 1.28–1.87 (m, 8H), 2.28 (t, 2H, J=7.3 Hz), 2.77 (t, 2H, J=7.3 Hz), 3.20 (t, 2H, J=7.0 Hz), 5.43 (s, 2H), 7.12–7.30 (m, 3H), 7.38–7.62 (m, 6H), 7.98–8.12 (m, 3H).

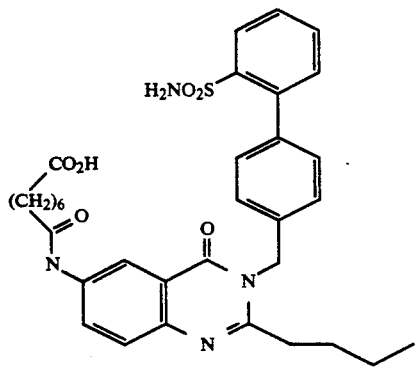

III-1-C-2

A solution of III-1-B-2. 60 mg in dimethyl suberate was heated at 140° C. for 4 hours. The reaction mixture was loaded onto Chromatotron and the intermediate methyl ester was isolated eluting with CH$_2$Cl$_2$/MeOH-30/1. The intermediate was saponified in ethanol (2 ml)/0.5M aq KOH (0.5 ml) at room temperature for 10 hrs. The reaction was diluted with water and washed with ethyl acetate. The aqueous layer was acidified and the product was extracted with ethyl acetate. Removal of the solvent in vacuo produced the crude product as colorless glass which was used for the macrocyclization step without further purification.

$^1$H-NMR (CDCl$_3$/CD$_3$OD-400 MHz): 0.92 (t, 3H, J=7.2 Hz), 1.33–1.48 (m, 6H), 1.56–1.65 (m, 2H), 1.66–1.76 (m, 4H), 1.26 (t, 2H, J=7.3 Hz), 2.38 (t, 2H, J=7.3 Hz), 2.91–2.98 (m, 2H), 5.47 (s, 2H), 7.23–7.28 (m, 3H), 7.42–7.58 (m, 4H), 7.73 (d, 1H, J=8.9 Hz), 8.07 (d, 1H, J=7.5 Hz), 8.15 (d, 1H, J=7.5 Hz), 8.41 (s, 1H).

IV: EXAMPLES

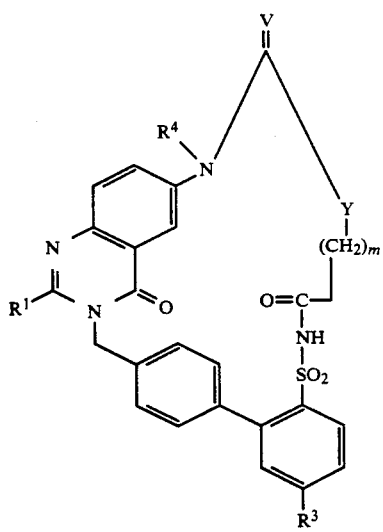

EXAMPLE IV-1

$R^1$=n-propyl; $R^4$=carbobenzyloxy; $R^3$=n-propyl; m=4; V=H$_2$ and Y=CH$_2$

To a solution of 68 mg (0.33 mmol) of dicyclohexylcarbodiimide, 0.12 g (0.99 mmol) of DMAP and 52 mg (0.33 mmol) of DMAP hydrochloride in 3 ml of dry, ethanol free chloroform at 70° C. was added over a period of 24 hours under N$_2$ 0.13 g (0.16 mmol) of II-1-F-2 dissolved in 5 ml of chloroform. The reaction mixture was diluted with 20 ml of CH$_2$Cl$_2$ and washed with 10% citric acid (1×5 ml), water (1×5 ml), brine (1×5 ml) and was dried over MgSO$_4$. The mixture was filtered and the filtrate was concentrated in vacuo and the residue was purified by radial chromatography over silica gel eluting with 50% EtOAc/hexanes to give the title product as a white solid. $^1$H-NMR (CDCl$_3$-400 MHz): 0.92 (t, 3H, J=7.3 Hz), 1.07 (t, 3H, J=7.4 Hz), 0.93 (m, 2H), 1.03 (m, 1H), 1.25 (m, 5H), 1.41 9 m, 2H), 1.61 (m, 4H), 1.91 9 m, 2H), 2.61 (t, 2H, J=8.0 Hz), 2.86 (t, 2H, J=7.7 Hz), 3.75 (t, 2H, J=6.6 Hz), 5.13 (s, 2H), 5.41 (s, 2H), 7.09 (m, 2H), 7.21–7.33 (m, 8H), 7.62 (bs, 1H), 7.69 (d, 1H, J=8.5 Hz), 8.02 (s, 1H), 8.12 (d, 1H, J=8.2 Hz).

Employing the procedures substantially as described for Example IV-1, but using the appropriate starting material, there were prepared the following:

EXAMPLE IV-2

$R^1$=n-propyl; $R^4$=carbobenzyloxy; $R^3$=H; m=4; V=H$_2$ Y=CH$_2$

Characteristic $^1$H-NMR (CDCl$_3$-400 MHz) signals: 1.08 (t, 3H, J=7.3 Hz), 1.92 (m, 2H), 2.87 (t, 2H, J=7.6 Hz), 3.76 (t, 2H, J=6.8 Hz), 5.13 (s, 2H, 5.40 (s, 2H), 7.09 (d, 2H, J=8.1 Hz), 7.21–7.33 (m, 6H), 7.55 9 m, 2H), 7.70 (d, 1H, J=8.6 Hz), 8.00 (d, 1H, J=1.6 Hz), 8.25 (m, 1H).

EXAMPLE IV-3

$R^1$=n-propyl; $R^4$=carbobenzyloxy; $R^3$=H; m=2; V=H$_2$ Y=CH$_2$

Characteristic $^1$H-NMR (CDCl$_3$-400 MHz) signals: 1.12 (t, 3H, J=7.2 Hz), 2.98 (t, 2H, J=7.9 Hz), 5.11 (s, 2H), 5.39 (s, 2H), 6.99 (bd, 2H, J=6.5 Hz), 7.15–7.31 (m, 7H), 7.49–7.61 (m, 3H), 7.74 (d, 1H, J=8.7 Hz), 7.92 (bs, 1H), 8.25 (dd, 1H, J=1.4, 7.8 Hz). 9.79 (bs, 1H).

EXAMPLE IV-4

$R^1$=n-butyl; $R^4$=carbobenzyloxy; $R^3$=H; m=4; V=H$_2$ Y=CH$_2$

Characteristic $^1$H-NMR (CDCl$_3$-400 MHz) signals: 0.99 (t, 3H), 2.99 (5, 2H, J=7.7 Hz), 3.45 (m, 4H), 3.81 (m, 2H), 5.15 (bs, 2H), 5.51 (bs, 2H), 7.16 (d, 2H, J=7.4 Hz), 7.30 (m, 8H), 7.55 (t, 1H, J=1.3 Hz), 7.65 (t, 1H, J=1.3 Hz), 8.02 (s, 1H), 8.15 (d, 1H, J=9.0 Hz).

EXAMPLE IV-5

$R^1$=n-propyl, $R^3$=H, $R^4$=H, V=CO, Y=NH, m=4

Characteristic $^1$H-NMR (CDCl$_3$/CD$_3$OD-400 MHz): 1.05 (t, J=7.3 Hz, 3H), 1.12–1.21 (m, 2H), 1.28–1.36 (m, 2H), 1.38–1.45 (m, 2H), 1.63–1.70 (m, 2H), 1.82–1.92 (m, 2H), 2.89 (t, 2H, J=8.5 Hz), 3.15–3.21 (m, 2H), 5.13–5.18 (m, 1H), 5.42 (s, 2H), 7.03 (d, 2H, J=7.7 Hz), 7.25–7.31 (m, 3H), 7.46–7.62 (m, 3H), 7.73 (d, 1H, J=7.6 Hz) 8.04 (d, 1H, J=2.6 Hz), 8.18 (d, 1H, J=8.0 Hz). FABMS m/e 588 (M+ +1).

EXAMPLE IV-6

$R^1$=n-butyl, $R^3$=H, $R^4$=H, V=CO, Y=CH$_2$, m=4

Characteristic $^1$H-NMR (CDC1$_3$/CD30D-400 MHz): 0.95–1.08 (m, 5H), 1.25–1.37 (m, 4H), 1.42–1.57 (m, 4H), 1.65–1.74 (m, 2H), 1.80–1.88 (m, 2H), 2.28–2.34

(m, 2H), 3.10-3.22 (m, 2H), 5.41 (s, 2H), 7.01-7.08 (m,2H), 7.17-7.27(m, 3H), 7.46-7.58 (m,2H), 7.66-7.71 (m, 1H), 7.82(d, 1H, J=7.8 Hz), 8.18(d, 1H, J=7.8 Hz), 8.43(b.s., 1H). FABMS m/e 601 (M++1).

EXAMPLE IV-7

$R^1$=n-butyl; $R^4$=H; $R^3$=H; m=4, V=$H_2$ Y=$CH_2$

A solution of 23 mg (0.03 mmol) of the product of Example IV-4 was hydrogenated under atmospheric pressure in 3 ml of MeOH in the presence of a catalytic quantity of 10% Pd/C over night. The reaction mixture was filtered and the filtrate was concentrated in vacuo and the residue was purified by flash chromatography over silica gel eluting with 2% MeOH/$CH_2Cl_2$ to give 15 mg of a white foam. $^1$H-NMR (CDCl$_3$-400 MHz): 1.07 (t, 3H, J=7.3 Hz), 1.17-1.40 (m, 4H), 1.53 (t, 2H, J=6.2 Hz), 1.67 (t, 2H, J=8.5 Hz), 1.85-2.03 (m, 4H), 2.87 (t, 2H, J=7.6 Hz), 3.29 (t, 2H, J=6.9 Hz), 4.02 (bs, 1H), 5.36 (s, 2H), 7.03 (dd, 1H, J=2.7, 8.7 Hz), 7.11 (d, 2H, J=7.7 Hz), 7.22-7.31 (m, 2H), 7.32 (d, 2H, J=7.7 Hz), 7.52-7.62 (m, 3H), 8.26 (dd, 1H, J=1.2, 7.8 Hz), 8.91 (bs, 1H).

EXAMPLE IV-8

$R^1$=n-butyl; $R^4$=benzoyl; $R^3$=H; m=4, V=$H_2$ Y=$CH_2$

A solution of 5 mg of the product of Example IV-7 was stirred over night in the presence of 10 uL of benzoyl chloride 10 uL of triethyl amine and a catalytic quantity of DMAP in 1 ml of $CH_2Cl_2$. The reaction mixture was diluted with 10 ml of EtOAc and washed with 10% citric acid (2×5 ml) and brine (1×5 ml) and dried over MgSO$_4$. The suspension was filtered and the filtrate was concentrated in vacuo and the residue was purified by chromatotron over silica gel eluting with 2% MeOH/$CH_2Cl_2$ to give 4.0 mg of title compound. $^1$H-NMR (CDCl$_3$-400 MHz): 0.95 (m, 2H), 1.07 (t, 3H, J=7.5 Hz), 1.03-1.12 (m, 2H), 1.21-1.38 (m, 4H), 1.48 (t, 2H, J=6.9 Hz), 1.59 (m, 2H), 1.89 (m, 2H), 2.85 (t, 2H, J=7.9 Hz), 3.98 (t, 2H, J=6.2 Hz), 5.37 (s, 2H), 7.03-7.61 (m, 14H), 7.90 (d, 1H, J=2.2 Hz), 8.08 (d, 1H, J=7.4 Hz), 8.26 (dd, 1H, J=1.2, 7.7 Hz).

EXAMPLE IV-9

$R^1$=n-propyl; $R^4$=H; $R^3$=n-propyl; m=4, V=$H_2$ Y=$CH_2$

The product of Example IV-1 was reduced in the manner described for Example IV-7 and the crude product was purified by chromatotron over silica gel eluting with 2% MeOH/$CH_2Cl_2$. $^1$H-NMR (CDCl$_3$-400 MHz): 0.93 (t, 3H, J=7.3 Hz), 1.07 (t, 3H, J=7.3 Hz), 1.07 (m, 2H), 1.18-1.39 (m, 6H), 1.53 (m, 2H), 1.60-1.72 (m, 4H), 1.89 (m, 2H), 2.61 (t, 2H, J=7.7 Hz), 2.86 (t, 2H, J=7.8 Hz), 3.98 (bs, 1H), 5.35 (bs, 2H), 7.02 (dd, 1H, J=2.8, 8.8 Hz), 7.09 (m, 2H, 7.20 (d, 1H, J=2.8 Hz), 7.31 (d, 2H, J=8.1 Hz), 7.50 (d, 1H, J=8.8 Hz), 8.14 (d, 1H, J=8.2 Hz), 8.83 (bs, 1H).

FORMULATION EXAMPLES

Typical Pharmaceutical Compositions Containing a Compound of the Invention

A: Dry Filled Capsules Containing 50 mg of Active Ingredient Per Capsule

| Ingredient | Amount per capsule (mg) |
|---|---|
| Example 1 | 50 |
| Lactose | 149 |
| Magnesium stearate | 1 |
| Capsule (size No. 1) | 200 |

Compound 1 can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain Compound 1 (25 mg), pregelatinized starch USP (82 mg), microcrystaline cellulose (82 mg) and magnesium stearate (1 mg).

C: Combination Tablet

A typical combination tablet would contain, for example, a diuretic such as hydrochlorothiazide and consist of Compound 1 (7.5 mg), hydrochlorothiazide (50 mg) pregelatinized starch USP (82 mg), microcrystalline cellulose (82 mg) and magnesium stearate (1 mg).

D: Suppository

Typical suppository formulations for rectal administration can contain Compound 1 (1-25 mg), butylated hydroxyanisole (0.08-1.0 mg), disodium calcium edetate (0.25-0.5 mg), and polyethylene glycol (775-1600 mg). Other suppository formulations can be made by substituting, for example, butylated hydroxytoluene (0.04-0.08 mg) for the disodium calcium edetate and a hydrogenated vegetable oil (675-1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectable formulation would contain Compound 1 (5.42 mg), sodium phosphate dibasic anhydrous (11.4 mg) benzyl alcohol (0.01 ml) and water for injection (1.0 ml). Such an injectable formulation can also include a pharmaceutically effective amount of another active ingredient such as another antihypertensive and/or a diuretic and/or an angiotensin converting enzyme inhibitor and/or a calcium channel blocker.

What is claimed is:

1. A compound of structural formula I:

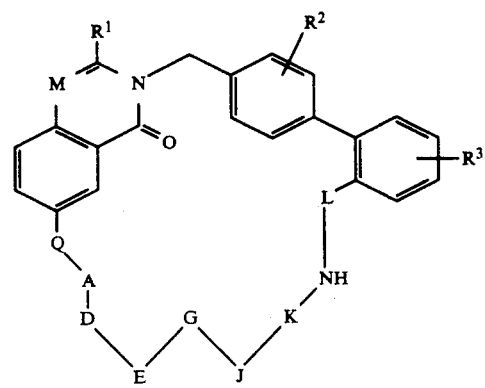

or a pharmaceutically acceptable salt thereof, wherein:

Q is —N(R⁴)— or

R¹ is
 a) aryl,
 b) $C_{1-6}$ alkyl or $C_{2-5}$ alkenyl, each of which is unsubstituted or substituted with aryl, $C_{3-7}$ cycloalkyl, halo, $CF_3$ or $CF_2CF_3$,
 c) $C_{3-7}$ cycloalkyl or
 d) perfluoro $C_{1-4}$ alkyl;
R² is $C_{1-6}$ alkyl or F;
R³ is
 a) H,
 b) $C_{1-6}$ alkyl,
 c) aryl,
 d) heteroaryl,
 e) $C_{1-4}$ alkylamino,
 f) di($C_{1-4}$ alkyl)amino,
 g) ($C_{1-6}$ alkoxy)$CH_2$—,
 h) ($C_{1-6}$ alkylthio)$CH_2$—,
 i) $C_{1-6}$ alkylthio,
 j) ($C_{1-6}$ alkyl)$_2NCH_2$—,
 k) $C_{2-6}$ alkenyl,
 l) $C_{2-6}$ alkynyl,
 m) aryl $C_{1-6}$ alkyl-, or
 n) $C_{3-7}$ cycloalkyl;
R⁴ is
 a) —COR⁶ wherein R⁶ is
  1) aryl,
  2) heteroaryl,
  3) morpholinyl,
  4) piperazinyl,
  5) N-($C_{1-4}$ alkyl)-piperazinyl,
  6) N-(aryl)piperazinyl
  7) $C_{1-6}$ alkyl, or
  8) substituted $C_{1-6}$ alkyl or

  9) N—(CR¹)-piperazinyl;

b) —CO₂R⁷ wherein R⁷ is
  1) $C_{1-6}$ alkyl
  2) substituted $C_{1-6}$ alkyl,
  3) aryl, or
  4) heteroaryl;
 c) —CONR⁷R⁸ wherein R⁸ is $C_{1-4}$ alkyl or H;
 d) $C_{1-6}$ alkyl,
 e) substituted $C_{1-6}$ alkyl,
 f) aryl, or
 g) heteroaryl;
 h) hydrogen,
M is —N= or

wherein R⁹ is H, $C_{1-3}$ alkyl, F or $CF_3$;
K is —CO— or —SO₂—;
L is —CO— or —SO₂—
A is —CO—, or —CH₂—;
D is —CH₂—, —O—, —NR⁸ or a single bond;
E is (CH₂)$_b$ wherein b=0–6;

G is (a) —C(R⁵)₂—, wherein the R⁵ groups are the same or different and R⁵ is $C_{1-6}$ alkyl, substituted $C_{1-6}$ alkyl, aryl, heteroaryl or hydrogen
 (b) —O—,
 (c) —S(O)$_p$— wherein p is 0–2,
 (d) —CH=CH—,
 (e) —CO—,
 (f) —NR⁵CO—,
 (g) —NHSO₂NH—,
 (h) —CO₂—,
 (i) —OCONH—,
 (j) —NHCO₂—,
 (k) —NR⁷,
 (l) aryl,
 (m) heteroaryl, or
 (n) single bond;
J is
 (a) (CH₂)$_r$, wherein r is 1–8, or
 (b) single bond
with the provisos that:
 1) if A is CO then R⁴ is $C_{1-6}$ alkyl, substituted $C_{1-6}$ alkyl, aryl, heteroaryl or H;
 2) if A is CO and D is O or NR⁸ then:
  (a) E is (CH₂)$_n$ wherein n is 2–6;
  (b) E is CH₂ and G is —C(R⁵)₂—; or
  (c) E is a single bond and G is aryl or heteroaryl;
 3) if A is —(CH₂)—, then R⁴ is —COR⁶, —CO₂R⁷, —CONR⁷R⁸ or H and D is —CH₂— or a single bond;
 4) if Q is piperazine then A is CO
wherein:
 aryl denotes phenyl or naphthyl, which can be unsubstituted or substituted with $C_{1-3}$ alkyl, $C_{1-3}$ alkoxy, halo, or $CF_3$; and
 heteroaryl means a 5- or 6-membered heteroaromatic comprising up to 3 heteroatoms selected from O, N and S selected from imidazole, pyrazole, triazole, thiazole, oxazole, thiadiazole, oxadiazole, oxathiazole, pyridine, pyrimidine, pyrazine, pyridazine, thiazine, wherein the heteroaromatic can be unsubstituted or substituted with one or two substituents selected from $C_{1-3}$ alkyl, $C_{1-3}$ alkoxy, halo or $CF_3$.

2. The compound of claim 1 or a pharmaceutically acceptable salt thereof wherein M is N.

3. The compound of claim 2 or a pharmaceutically acceptable salt thereof wherein L and K are independently —SO₂ or —CO—.

4. The compound of claim 3 or a pharmaceutically acceptable salt thereof wherein A is —CH₂— or —CO—.

5. The compound of claim 4 or a pharmaceutically acceptable salt thereof selected from the group consisting of the following compounds:

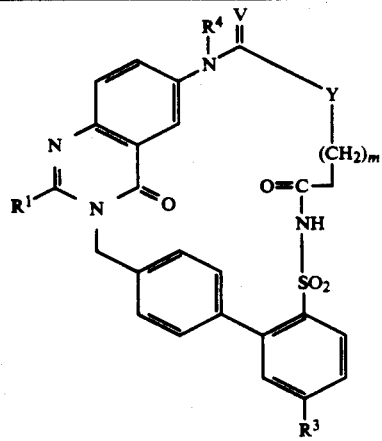

| R¹ | R³ | R⁴ | m | V | Y |
|---|---|---|---|---|---|
| n-propyl | n-propyl | -carbobenzyloxy | 4 | H₂ | CH₂ |
| n-propyl | H | carbobenzyloxy | 4 | H₂ | CH₂ |
| n-propyl | H | carbobenzyloxy | 2 | H₂ | CH₂ |
| n-butyl | H | carbobenzyloxy | 4 | H₂ | CH₂ |
| n-butyl | H | H | 4 | H₂ | CH₂ |
| n-butyl | H | benzoyl | 4 | H₂ | CH₂ |
| n-propyl | n-propyl | H | 4 | H₂ | CH₂ |
| n-propyl | H | H | 4 | CO | NH |
| n-butyl | H | H | 3 | CO | CH₂ |

6. A pharmaceutical composition useful in the treatment of hypertension which comprises a pharmaceutically acceptable carrier and a pharmaceutically effective amount of a compound of claim 1.

7. The composition of claim 6 which includes another antihypertensive selected from a diuretic selected from hydrochlorothiazide, chlorothiazide, chlorthalidone, methyclothiazide, furosemide, ethacrynic acid, triamterene, amiloride and spironolactone; a calcium channel blocker, selected from diltiazem, felodipine, nifedipine, nitrendipine and verapamil; a β-adrenergic antagonist selected from timolol, atenolol, metoprolol, propanolol, nadolol and pindolol; an angiotensin converting enzyme inhibitor selected from enalapril, lisinopril, captopril, ramipril, quinapril and zofenopril; a renin inhibitor selected from A-69729 and FK 744; an α-adrenergic antagonist selected from prazosin, doxazosin, and terazosin; a sympatholytic agent selected from methyldopa, clonidine and guanabenz; the atriopeptidase inhibitor, UK-79300; the serotonin antagonist, ketanserin; the A₂-adenosine receptor agonist CGS 22492C; a potassium channel agonist selected from pinacidil and cromakalim; or another antihypertensive drug selected from reserpine, minoxidil, guanethidine, hydralazine hydrochloride and sodium nitroprusside; or combinations of the above-named drugs.

8. A method of treating hypertension which comprises administering to a patient in need of such treatment a pharmaceutically effective amount of a compound of claim 1.

9. An ophthalmological formulation for the treatment of ocular hypertension comprising an ophthalmologically acceptable carrier and an effective ocular antihypertensive amount of a compound of claim 1.

10. A method of treating ocular hypertension comprising administering to a patient in need of such treatment an effective ocular antihypertensive amount of a compound of claim 1.

* * * * *